United States Patent
Iftime et al.

(10) Patent No.: US 11,994,474 B2
(45) Date of Patent: May 28, 2024

(54) PRINTED SENSOR WITH VIBRANT COLORIMETRIC PARTICLES

(71) Applicant: Palo Alto Research Center Incorporated, Palo Alto, CA (US)

(72) Inventors: Gabriel Iftime, Newark, CA (US); Mahati Chintapalli, Mountain View, CA (US); Eli Bulger, Nottawa (CA); Warren Jackson, San Francisco, CA (US); Sean Emerson Doris, San Francisco, CA (US); Jessica Louis Baker Rivest, Palo Alto, CA (US); Eric Cocker, Redwood City, CA (US); Antonio Williams, Concord, CA (US); Crystal Pham, Anaheim, CA (US)

(73) Assignee: XEROX CORPORATION, Norwalk, CT (US)

( * ) Notice: Subject to any disclaimer, the term of this patent is extended or adjusted under 35 U.S.C. 154(b) by 2 days.

(21) Appl. No.: 18/115,364

(22) Filed: Feb. 28, 2023

(65) Prior Publication Data
US 2023/0228687 A1    Jul. 20, 2023

Related U.S. Application Data

(62) Division of application No. 16/227,807, filed on Dec. 20, 2018, now Pat. No. 11,614,409.

(51) Int. Cl.
*G01N 21/78*    (2006.01)
*G01N 33/52*    (2006.01)

(52) U.S. Cl.
CPC .......... *G01N 21/78* (2013.01); *G01N 33/525* (2013.01)

(58) Field of Classification Search
CPC ...... G01N 21/78; G01N 33/525; G01N 33/52; G01N 21/6447; G01N 2021/7786; G01N 21/29
See application file for complete search history.

(56) References Cited

U.S. PATENT DOCUMENTS

| | | | |
|---|---|---|---|
| 5,723,554 A | 3/1998 | Fujita | |
| 5,795,557 A | 8/1998 | Pajonk et al. | |
| 6,713,584 B1 | 3/2004 | Chisholm et al. | |
| 7,732,496 B1 | 6/2010 | Leventis | |

(Continued)

FOREIGN PATENT DOCUMENTS

| | | |
|---|---|---|
| EP | 3502670 A1 | 6/2019 |
| KR | 101792363 B1 | 10/2017 |

(Continued)

OTHER PUBLICATIONS

Zhang, et al. Polymer Nanofibers with Outstanding Thermal Conductivity and Thermal Stability: Fundamental Linkage Between Molecular Characteristics and Macroscopic Thermal Properties, Journal of Physical Chemistry C 2014 118:36, pp. 21148-21159.
Jenkins et a. "Terminology for reversible-deactivation radical polymerization previously called 'controlled' radical or living' radical polymerization (IUPAC Recommendations 2010," Pure Applied Chemistry, vol. 82, No. 2, pp. 483-491, 2010.

(Continued)

*Primary Examiner* — Samuel P Siefke
(74) *Attorney, Agent, or Firm* — Miller Nash LLP (57) ABSTRACT

A method of forming a colorimetric sensor includes depositing a first material onto a substrate, providing porous sensing particles, wherein the sensing particles comprise sensing species dispersed into a porous host structure, and embedding the porous sensing particles onto a surface of the deposited first material, the first material attaching the sensing particles to the substrate with at least a portion of the sensing particles is exposed to an ambient environment.

16 Claims, 4 Drawing Sheets

(56) References Cited

U.S. PATENT DOCUMENTS

| | | | |
|---|---|---|---|
| 7,897,057 | B1 | 3/2011 | O'Connor et al. |
| 8,663,742 | B2 | 3/2014 | Kissel |
| 2003/0013822 | A1 | 1/2003 | Chisholm et al. |
| 2004/0063880 | A1 | 4/2004 | Chisholm et al. |
| 2010/0163157 | A1 | 7/2010 | Mulburn |
| 2011/0237692 | A1 | 9/2011 | Wu et al. |
| 2011/0311802 | A1 | 12/2011 | Cho |
| 2014/0065329 | A1 | 3/2014 | Showers |
| 2014/0080934 | A1 | 3/2014 | Wu et al. |
| 2019/0106543 | A1 | 4/2019 | Chintapalli et al. |
| 2020/0031977 | A1 | 1/2020 | Chintapalli et al. |
| 2020/0200684 | A1 | 6/2020 | Iftime et al. |

FOREIGN PATENT DOCUMENTS

| | | |
|---|---|---|
| WO | 9946310 A1 | 9/1999 |
| WO | 2010080238 A3 | 7/2010 |

OTHER PUBLICATIONS

Belmares et al., "Hildebrand and Hansen Solubility Parameters from Molecular Dynamics with Applications to Electronic Nose Polymer Sensor Polymers," Wiley Periodicals 2004.

Graeme Mood et al., "A Micro Review of Reversible Addition/Fragmentation Chain Transfer (RAFT) Polymerization," Sigma-Aldrich, 8 pages.

Sebastien Perrier, "50th Anniversary Perspective: RAFT Polymerization—A User Guide," Macromolecules 2017, 50, pp. 7433-7447.

Vivek Mishra, "Living Radical Polymerization—A Review," Journal of Scientific Research, vol. 56, 2012 pp. 141-176.

Dolai et al., "Colorimetric Polydiacetylene-Aerogel Detector for Volatile Organic Compounds (VOCs)," ACS Applied Materials & Interfaces, vol. 9, No. 3, Jan. 10, 2017, pp. 2891-2898.

Li, "Nanoporous Silica-Dye Microspheres for Enhanced Colorimetric Detection of Cyclohexanone," Chemosensors MDPI Switzerland, vol. 6, No. 3, Aug. 13, 2018, p. 34 (11 pages).

PRINTED SENSOR WITH VIBRANT COLORIMETRIC PARTICLES

RELATED APPLICATION

This application is a divisional of, and claims priority to, U.S. patent application Ser. No. 16/227,807 filed Dec. 20, 2018, which is incorporated herein by reference in its entirety.

TECHNICAL FIELD

This disclosure relates to colorimetric sensors, more particularly to printed colorimetric sensors.

BACKGROUND

Colorimetric sensors change color when exposed to particular substances or conditions, such as toxic chemicals, heat, cold, light, pathogens, and chemical warfare gases, for example. These sensors will play a key role in several markets including smart packaging that can monitor product freshness, environmental monitoring, and military and industrial applications.

Figure 1:
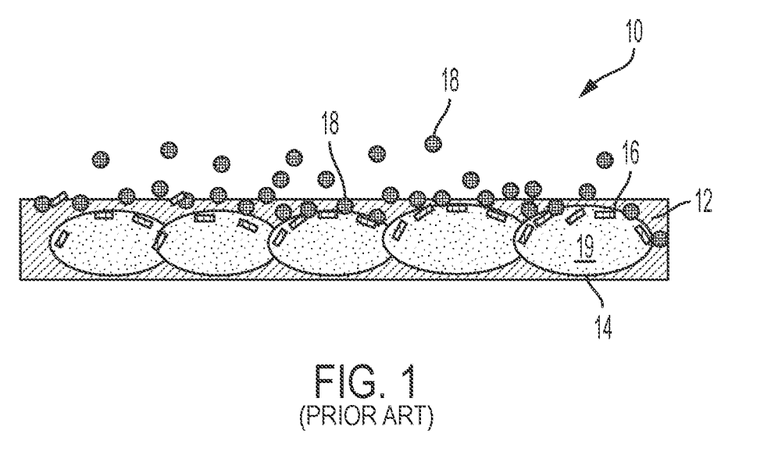
FIG. 1 shows an embodiment of a prior art colorimetric sensor.

Many of these applications, particularly in smart packaging, require custom printed sensors with functional colorimetric inks at the time of product packaging. These inks generally consist of particles containing dispersed sensing species for detecting a particular substance or condition. FIG. 1 shows a prior art embodiment of a printed colorimetric sensor 10 incorporating sensing particles. The printed colorimetric sensor 10 consists of a polymer binder 12 into which are dispersed sensing particles 14. The polymer binder 12 holds the sensing particles 14 in place after printing. The sensing particles 14 contain sensing species 16 dispersed into a dense support material 19. During printing, the polymer binder and the sensing particles 14 containing the sensing molecules 16 are mixed with a solvent to allow printing. After printing, solvent evaporation produces a dense polymer layer fully covering the sensing particles 14. The sensing species 16 change color when in the presence of the analyte 18. With this prior art design, the detection is limited in two ways. First, the access of analyte 18 is slowed down or blocked by the dense polymer binder 12. Second, after some of the molecules 18 penetrate through the polymer binder layer 12, the detection is further limited to the top surface of the sensing particles 14 of the printed sensor because only the top surface sensing species receive exposure to the compound being detected. The dense support material 19 blocks access for the sensing species 16 placed deeper in the layer (not shown), so the analyte 18 does not reach them.

These limitations result in slow response times and poor detection of trace analytes. These limitations are a result of slow diffusion of the analyte through the dense binder and particle materials. As a result, the sensor has a small degree of color change that is difficult to detect directly with the human eye. Spectral analysis with sensitive spectroscopic equipment may address the issue, but increases the cost and power requirements of the overall detection system and limits system portability.

SUMMARY

A method of forming a colorimetric sensor includes depositing a first material onto a substrate, providing porous sensing particles, wherein the sensing particles comprise sensing species dispersed into a porous host structure, and embedding the porous sensing particles onto a surface of the deposited first material, the first material attaching the sensing particles to the substrate with at least a portion of the sensing particles is exposed to an ambient environment.

A method of forming a colorimetric sensor includes depositing a first material onto a white substrate, providing porous sensing particles, wherein the sensing particles comprise color changing sensing species that change color in the presence of an analyte dispersed into a porous host structure, and embedding the porous sensing particles onto a surface of the deposited first material, the first material attaching the sensing particles to the substrate with at least a portion of the sensing particles is exposed to an ambient environment.

According to aspects illustrated here, there is provided a method of forming a colorimetric sensor that includes depositing a first material onto a dark substrate, providing porous sensing particles, wherein the sensing particles comprise fluorescence changing sensing species that change their fluorescence in the presence of an analyte dispersed into a porous host structure, and embedding the porous sensing particles onto a surface of the deposited first material, the first material attaching the sensing particles to the substrate with that at least a portion of the sensing particles is exposed to an ambient environment.

DETAILED DESCRIPTION OF THE EMBODIMENTS

As used here, the term 'colorimetric' means a substance that changes color when exposed to a particular material or condition, and 'vibrant colorimetric sensor' means a sensor of which some portion changes color when exposed to the material or condition and the color change is noticeable enough to allow detection by a human eye. Color change means a change in the intensity or wavelength of light absorption, transmission, reflection, fluorescence, or phosphorescence, in the near-ultraviolet to near-infrared wavelengths of 200-4000 nanometers, or in the range of 200-800 nm.

As used here, the term 'high transparency' and its related terms such as 'transparent,' or 'highly transparent' means a material having a visible light transmittance of at least 20% or higher over a path length of 3 millimeters or more in the discolored state. Similarly, the term 'low haze' means a material of lower haze than 15% per millimeter. The term 'porous,' 'highly porous,' and 'high porosity' and their related terms means that the material has a porosity of at least 10%.

As used here, the term porous host or porous host structure means a material that contains void within its structure. The voids create porosity within the structure and provide an internal surface area.

As used here, the term 'aerogel' means one possible type of porous host substrate material with high porosity, high internal specific surface area, and an open pore structure permeable to gases. 'Open pore structure' means have pores which are interconnected throughout the bulk of the material so that gases or liquids can permeate through the material. Aerogels are produced by forming a network, for example a crosslinked polymer gel, a silica gel, or interconnecting fibers, in a liquid solution, and removing the liquid, leaving behind open porosity. Aerogels typically have Brunauer Emmett Teller surface areas above 50 $m^2/g$, as measured by $N_2$ adsorption porosimetry. In one embodiment the aerogel of or other host structure has a specific surface area of at least 100 $m^2/g$.

Figure 2:
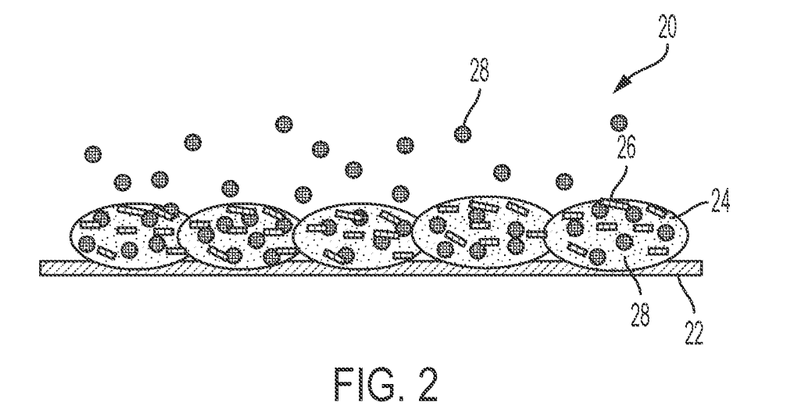
FIG. 2 shows an embodiment of a colorimetric sensor.

The embodiments described herein include colorimetric sensors having porous sensing particles deposited onto the surface of a pre-deposited pattern, typically of ink, where at least portions of the sensing particles receive direct exposure to the ambient environment. The pre-deposited pattern may be deposited directly onto a surface such as a substrate, and attach the sensing particles to the surface. In some of the embodiments, the sensing particles consist of sensing species dispersed into a porous host structure. In one embodiment the host structure may be an aerogel that may be a transparent, low haze, high surface area, porous, aerogel. The aerogel will typically comprise a polymer aerogel, but may comprise inorganic aerogels, such as silica aerogels. Other host structures may include metal oxides which are sometimes considered as ceramic materials. Suitable metal oxide host materials include silicon dioxide $SiO_2$, aluminum oxide $Al_2O_3$, tin oxide $SnO_2$, titanium dioxide $TiO_2$, and zirconium dioxide ($ZrO_2$). Organic-inorganic hybrid aerogels are also suitable. They are typically obtained by incorporating alkylalkoxy precursors which are not hydrolysable during aerogel formation. As an example, in the case of silica aerogel fabrication suitable alkylalkoxy precursors include alkyl triethoxy or trimethoxy silanes. Examples include methyltriethoxysilane, methyltriethoxysilane, ethyltriethoxysilane, hexyltriethoxysilane and others. FIG. 2 shows an embodiment of a printed, vibrant, colorimetric sensor 20. The sensor consists of layer 22 on the substrate. In one embodiment, layer 22 is directly on, and in contact with, the substrate. The substrate may be paper, plastic, wood, polymers, glass, metal, ceramic, fabric, adhesive tape, cardboard etc., and may consist of part of the packaging of an object, part of the object itself, or a separate tag or other type of external surface.

When deposited onto a packaging material, the colorimetric sensor may be printed. Printing may enable specific messages such as for example, warnings or indicators for when packaged food becomes spoiled or not edible. The printed colorimetric sensor may be inside or outside the packaged product. Printing is performed by depositing a first material onto the surface of the packaging substrate followed by placing sensing particles onto the first material and curing in such a way that the first material keeps the sensing species attached to the surface of the packaging substrate in such a way that at least a portion of the sensing particles is exposed to the ambient environment. When printing, the first material may be an ink such an inkjet curable ink such as UV curable or thermally curable. The ink may also be a conventional inkjet ink that solidifies by solvent evaporation in order to keep the colorimetric particles attached to the packaging substrate.

The surface may be flat or the boundary of a three-dimensional object. The layer 22 has on its surface a layer of sensing particles 24. In this embodiment, the sensing particles 24 comprise a porous, transparent aerogel support material 29. The support material contains sensing species 26 dispersed throughout the volume or internal surface area of sensing particles 24. At least a portion of the sensing particles is exposed to an ambient environment.

The embodiments here solve the prior art limitations because it allows unrestricted access of the analyte 28 through the depth of the particles to activate many more sensing species 26 and as such enables high coloration, fast response and low limit of detection.

In one embodiment, the sensing species comprise molecules of a material that changes color in the presence of the analyte 28 to be detected. In other embodiments, the sensing species comprises inorganic complexes, nanoparticles, salts, organic molecules, polymers, or combinations thereof that change color in the presence of the analyte 29. The interaction between the sensing species and analyte may be chemical, such as the formation/breaking of covalent bonds, oxidation/reduction, protonation/deprotonation, etc., or physical, such as adsorption, dissolution, phase change, etc. referred to here as being chemically reactive. Examples of sensing species may include pH indicators, such as bromocresol green, phtalocyanine dye, porphyrin dies, indigo derivatives, azo dyes, anthraquinone dye, triarylmethane dye, and fluorescent and phosphorescent dyes.

Other sensing species may include transition metal salts that coordinate with evolved gases including palladium chloride, palladium sulfates, ammonium molybdates, and potassium permanganate. The above materials are provided as examples and not intended to limit the scope of the embodiments.

The detection process may occur by several mechanisms. In a first mechanism, the sensor is in a discolored state in its inactive state and switches to a colored state when activated by the analyte. In a second mechanism, the sensor is colored in the absence of the analyte and discolors when the analyte is present. A third mechanism would be a change from one color to another. A fourth mechanism would be a change in the emissive properties of the sensor, such as a change in the phosphorescence or fluorescence emission color, intensity, time constant, etc. Fluorescent sensors change the characteristics of emitted fluorescent light when examined under black light as a result of a chemical reaction or a physical interaction with an analyte. The characteristics that are subject to change upon interaction with the analyte include the intensity and the wavelength, therefore the color of the emitted light.

Multiple situations are possible with fluorescent detection. In a first case, the material in non-fluorescent in the absence of the analyte and becomes fluorescent, i.e. emit a specific color light when examined with black light, a type of UV light. In a second case, the material is fluorescent in the absence of the analyte and loses fluorescence after chemical or physical interaction with the analyte. Another case is when the wavelength and therefore the color of the emitted fluorescent light changes upon interaction with the analyte.

Any combination of these mechanisms can operate in a colorimetric sensor.

A colorimetric sensor may function as an instantaneous sensor or an integrating sensor. In an instantaneous sensor, the coloration response is correlated to the current or recent concentration of the analyte. In an integrating sensor, the coloration response is related to the cumulative exposure to the analyte or condition.

The aerogel matrix may be passive or active in the detection of the analyte or environmental condition. For example, the aerogel matrix may be active if it assists in adsorbing the analyte, if it enables selective permeability of some analyte but not others, or if it contributes some other property not specific to the sensing molecule.

Figure 3:
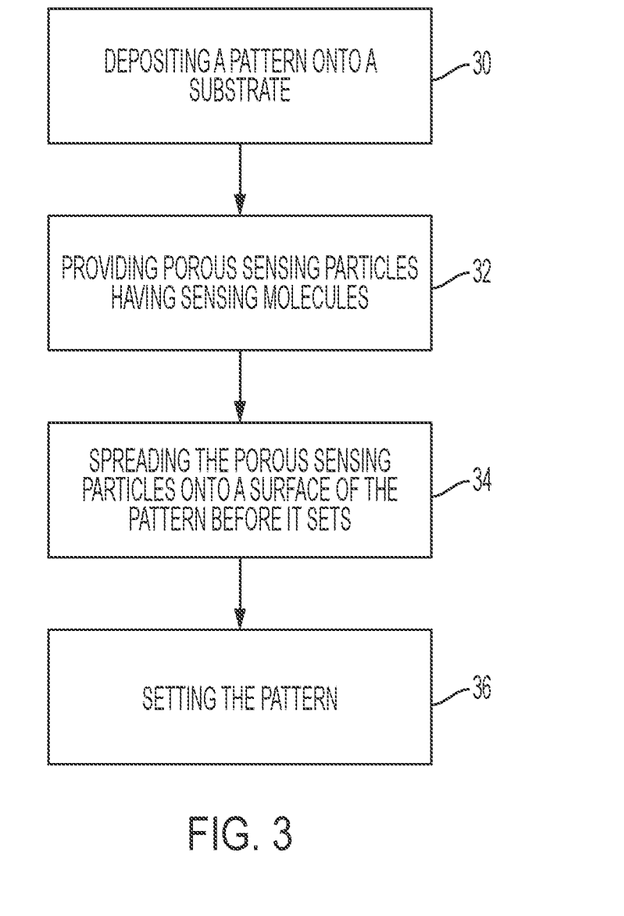
FIG. 3 shows a flowchart of an embodiment of manufacturing a vibrant colorimetric sensor.

A sensor such as those shown in FIG. 2 may result from a manufacturing process as shown in FIG. 3. At 30, the process starts by depositing a pattern on the substrate. The pattern may be formed of wet or curable ink. "Ink" as used here means any liquid capable of being deposited onto a surface and then dried, solidified, polymerized or otherwise cured. The ink may be deposited onto the substrate by one of many methods including inkjet printing, screen printing, spray-coating, doctor blading, slot die coating, or lamination of a free-standing adhesive filament or film onto a substrate, among many others. The ink or substrate may be selected to enhance the colorimetric response of the sensor by increasing the reflectivity, contrast, or perceived color change. As an example, a white substrate may enhance the colorimetric response in the case of a color changing sensor that changes from a colorless or a lower coloration state to a darker colored state upon interaction with the analyte. As an another example, a black or dark substrate material is preferred generally for maximizing the intensity of the emitted light in the case of fluorescent of phosphorescent materials. In this case a white substrate would typically scatter or even produce additional blue emitted light which would affect the fluorescence emitted as a result of the analyte detection.

Prior to or during the deposition of the ink pattern, the process provides porous sensing particles that have sensing species at 32. Typically, aerogels form monolithic structures and have to undergo some sort of process to make particles. This may include grinding or milling. However the aerogel is broken up, the process will be referred to here as grinding. In some instances, the addition of a dispersant at the time of particle grinding provided improved quality in the printing of the particles by improving particle spreadability onto the printed pattern and minimizing particle aggregation. The size of the particles resulting from grinding can be controlled by processing parameters such as the type and the size of grinding media, grinding time, and grinding speed, which may be expressed as rotations per minute. A preferred grinding media includes zirconium oxide media because it does not affect the color of the grinded particles. Any size of the grinding media may be suitable, such as for example from 1 mm to 10 mm.

In an alternative embodiment, the particles may be manufactured by direct synthesis of the particles through emulsion polymerization, spray, atomization, or precipitation techniques. In this embodiment, the particle size may be controlled by various means such as solvent type, support material or support materials precursors, concentration, processing temperature, further grinding, and other means.

The sensing species can be incorporated into the porous particles in a variety of ways. These include infusing the aerogel with the sensing species from a solution, either prior to or after grinding, having sensing species present in the solvent at the time of gel formation from the precursors, and chemically grafting the sensing species onto polymer or silica walls during or after the formation of the aerogel, among others. The resulting sensor has porous particles exposed directly to the environment, therefore the analyte has unrestricted access to the sensing species through air into the depths of the porous particles.

At 34, the porous sensing particles were spread onto a surface of the pattern before it sets. The ink may be a curable composition, such that the surface remains tacky and allows the particles to stick to its surface, or the process may just spread the particles before the ink dries. After spreading the particles, the process then sets the pattern in step 36, either by curing or drying the ink. In the case where a UV-curable ink is used, the thickness of the tacky layer may be controlled by exposing the surface to $O_2$, which inhibits curing. The thickness of the tacky layer determines the quantity of sensing particles that can be adhered to the surface as well as the level of exposure of the particles to the ambient atmosphere.

Example 1

A porous polymer gel monolithic block was obtained by a procedure such as that disclosed in U.S. patent application Ser. No. 15/728,385. The process of forming the aerogel, which may consist of a radical crosslinked polymer network, may comprise one of many different processes, including, but not limited to radical polymerization processes, which includes controlled radical polymerization processes such as stable free radical polymerization (SFRP), atom transfer radical polymerization (ATRP), reversible addition-fragmentation chain transfer (RAFT), and the use of chain transfer agents.

In typical processes for forming an aerogel, such as those disclosed in U.S. patent application Ser. Nos. 16/046,692 and 15/728,385, polymerizable precursors are dissolved in a high boiling point good solvent along with an initiator and optionally polymerization control agents. A good solvent is one where the Flory-Huggins interaction parameter between the solvent and the polymer gel network is below 0.5, or one where the difference in Hildebrand solubility parameters between solvent and polymer is below 1. A high boiling point solvent is one with a boiling point above the polymerization temperature, typically 50-150° C. The amount of polymerizable precursor ranges from 0.1-60 wt % of the precursor solution. The amount of solvent ranges from 40-99.9 wt % of the precursor solution. The amount of initiator ranges from 0.001-10 wt % of the precursor solution. The amount of control agent ranges from 0.001-10 wt % of the precursor solution. Precursors consist of vinyl monomers and crosslinkers, wherein at least 30% of the precursors by mass are stiff. A component is stiff if it has a Young's Modulus of 3.5 GPa or greater when polymerized by itself as a homopolymer.

Examples of stiff precursors comprise divinylbenzene, trimethacryladamantane, hexanedioldiacrylate, hexanedioldimethacrylate, ethylene glycol dimethacrylate. For a chain transfer agent controlled process, the control agent comprises one or more of: an organic thiol chain transfer agent, dodecanethiol, chloroform, octyl mercaptan, or 1,8-dimercapto-3,6-dioxaoctane. For an SFRP process, the control agent comprises one of: a stable nitroxide, an alkoxyamine, a stable nitroxide derived from decomposition of an alkoxyamine, 2,2,6,6-Tetramethyl-1-piperidinyloxy (TEMPO), or 4-hydroxy-TEMPO. In addition to a stable radical, control agents such as reducing agents (comprising one or more of hydroxyacetone, ascorbic acid, glucose, ene-diol species) or time-controlled decomposing radicals (radicals that have a decomposition half-life longer than an hour in the reaction conditions which include solvent and temperature) may be used. For a RAFT process, the control agent may comprise: trithiocarbonates, xanthates, or benzodithioates. For an ATRP process, the control agent may comprise a transition metal redox center complexed with ligands such as amine-functional ligands. Polymerization is carried out in a deoxygenated environment for 1 min to 72 hrs at temperatures ranging from 50-150° C. In some cases, photoinitiaton may also be used. In such polymerizations, the temperature can be as low as room temperature (18° C.).

At the end of the polymerization process the solvent was exchanged with a solvent that can dissolve the sensing molecule of interest such as benzene, ethanol, diethylether, or acetone. The wet, monolithic block was then placed in a solution containing bromocresol green dye, a pH indicator, in solvent and allowed to set for two days. This produced a wet gel that contains embedded colorimetric dye within its pores. The solvent was slowly evaporated at room temperature then the porous structure was dried overnight in vacuum to complete solvent evaporation.

The wet monolithic gel can also be crushed before the solvent exchange with the sensing material solution to decrease the diffusion time for sensing material to penetrate the gel.

The monolithic aerogel block containing dye was then placed in a planetary ball mill with 3 mm zirconia beads and ground to produce porous particles incorporating sensing dye within pores. The particles were separated by sieving and the different particle size fractions were collected separately. The fraction of particles less than 53 micrometers (microns) was used for printing. Alternatively, grinding with a coffee maker device produced only very large particles, on the orders of hundreds of microns, which are not suitable for high resolution prints.

Experiments were also performed where grinding of the dry aerogel materials was performed with the addition of small amounts of a polar surfactant dispersant PEO-PE (poly(ethylene oxide)-polyethylene) (0.1-30% by mass with respect to the sensing particles with dye). Table 1 shows that the mass fraction of collected particles with a particle size of less than 53 microns is increased from 78% to 95%, providing the beneficial effect of the additive for reducing the particle aggregation.

| | Fraction of <53 micron recovered particles |
|---|---|
| Aerogel w/o additive | 78% |
| Aerogel with 0.1-10% PEO-PE additive | ≥95% |

Example 2

A clear aerogel material was prepared by mixing tetramethylorthosilicate (10.4 g) with methyl triethoxysilane (9.3 g) in 25 g methanol and 6.2 g water. The mixture was stirred for 12 hours. Droplets of ammonia solution in water were added gradually until the pH reached 9.0. The mixture was allowed to stand for 48 hours. The solvent was then exchanged with acetone (2 times, 12 hours each).

The cured wet gel was broken into smaller pieces and immersed in a solution consisting of 1.5 g bromocresol green dissolved in 215 ml of acetone. The solution was dark blue in color. Small amounts of hydrochloric acid were added gradually until the dark coloration disappeared to produce a clear light yellow solution. After stirring for 24 hours, the wet pieces were removed from the solution and allowed to slowly dry in a container with a small hole on its lid, which allows for very slow evaporation, for two weeks. The dry material was then subjected to ball milling similar to the process of Example 1.

Example 3

A layer of commercially available UV curable ink was deposited onto a PET plastic substrate using a doctor blade. In another example, a gel UV curable ink was printed with an inkjet printer. Sensor particles, such as those produced in Examples 1 and 2, were then spread onto the surface of the UV curable inks, where they adhered. Curing was performed by exposure to a UV light at 365 nanometer wavelength. Any particles that do not stick to the surface were then collected and recycled.

Example 4

Sensor Testing

Figure 4:
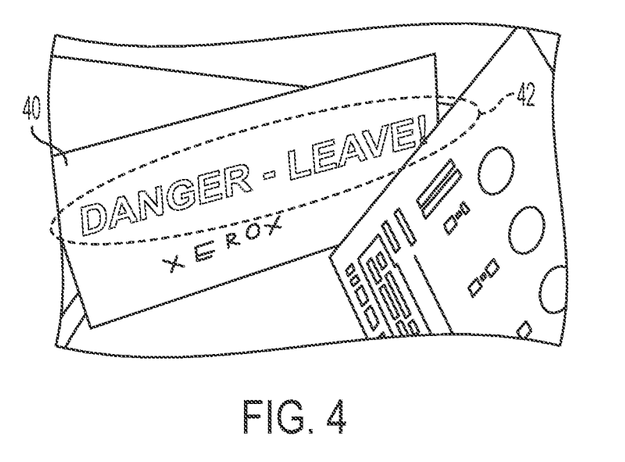
FIG. 4 shows an embodiment of a previously unused vibrant colorimetric sensor prior to exposure.
Figure 5:
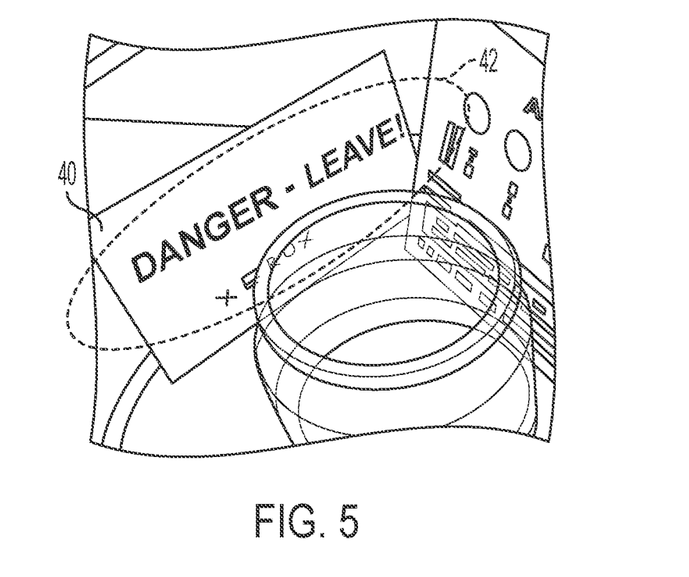
FIG. 5 shows an embodiment of a vibrant colorimetric sensor after being exposed to a contaminant.

A sensor, shown in FIG. 4, manufactured as described in Examples 1-3 was exposed to ammonia gas. The message 42 printed on the sensor colored as shown in FIG. 5, very quickly, in less than 2 seconds. In contrast, a commercially-available ammonia badge, ChromAir Ammonia Safety Badge (Morphix Part #380003-10) took approximately 40 seconds for a coloration detectable by eye.

Sensors made in a similar way as in Examples 1-3, were placed in the proximity of isopropyl amine, a common VOC (volatile organic compound). The printed sensor manufactured in accordance with the embodiments described herein colored in seconds while the commercial sensor did not color even after 3 hours of continuous exposure to isopropyl amine vapors.

Example 5

Figure 6:
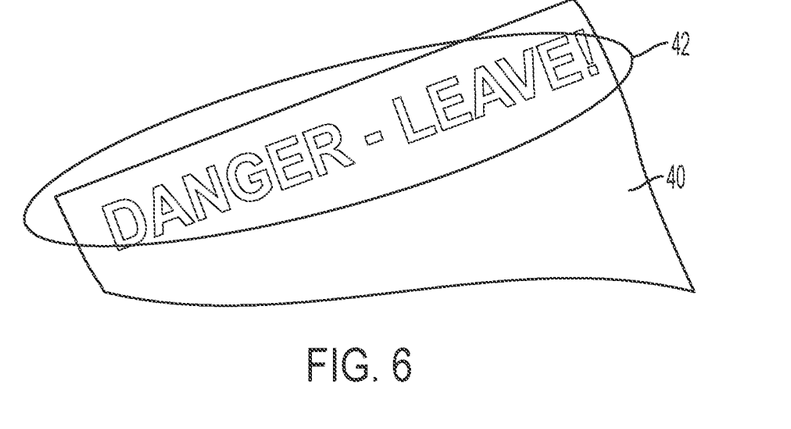
FIG. 6 shows an embodiment of a reversible vibrant colorimetric sensor after being exposed to a reversing agent.

A sensor manufactured as described in Examples 1-3 was exposed to ammonia vapors and colored as described in Example 4. Next, the colored sensor was exposed to hydrochloric acid vapors and it discolored in about 10-15 seconds as shown in FIG. 6. The coloration/discoloration cycle was repeatable. This illustrates sensor reversibility and its potential use for being re-usable instead of common commercially available sensors that are generally single use sensors. Other sensors may be irreversible.

In this manner, one can manufacture digitally printed, vibrant, colorimetric sensors with enhanced coloration when compared with the current state-of-the-art. These sensors have fast response and increased sensitivity when compared with commercially available sensors and can be printed on demand at the time of product packaging.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method of forming a colorimetric sensor, comprising:
   depositing a first material onto a substrate;
   providing porous sensing particles, wherein the sensing particles comprise sensing species dispersed into a porous host structure;
   embedding the porous sensing particles onto a surface of the deposited first material, the first material attaching the sensing particles to the substrate with at least a portion of the sensing particles is exposed to an ambient environment; and
   one of either curing or drying the first material after providing the porous sensing particles to set a deposited pattern.

2. The method of claim 1, wherein depositing the first material comprises printing the pattern with an ink.

3. The method of claim 1, wherein one of either the ink or the substrate are chosen to enhance a perceived color change of the sensor.

4. The method of claim 1, wherein providing porous sensing particles includes:
   forming a porous aerogel;
   performing one of breaking up the porous aerogel or directly synthesizing the porous aerogel to form particles of porous aerogel structures; and
   adding sensing species to the porous aerogel.

5. The method of claim 4, wherein forming the porous aerogel comprises forming the porous aerogel by one method selected from the group consisting of: stable free radical polymerization, atom transfer radical polymerization, reversible addition-fragmentation chain transfer, and the use of chain transfer agents.

6. The method of claim 4, wherein adding sensing species comprises infusing the aerogel with the sensing species.

7. The method of claim 4, wherein adding the sensing species comprises having the sensing species present in a solvent that is a part of a precursor solution used to form the aerogel.

8. The method of claim 4, wherein adding the sensing species comprises chemically grafting the sensing species onto aerogel walls during or after forming the aerogel.

9. The method of claim 4, wherein the aerogel one of either adsorbs an analyte of interest or selectively adsorbs the analyte of interest over other substances.

10. A method of forming a colorimetric sensor, comprising:
    depositing a first material onto a white substrate;
    providing porous sensing particles by one of infusing the aerogel with the sensing species, having the sensing species present in a solvent that is a part of a precursor solution used to form the aerogel, or chemically grafting the sensing species onto aerogel walls during or after forming the aerogel, wherein the sensing particles comprise color changing sensing species that change color in the presence of an analyte dispersed into a porous host structure; and
    embedding the porous sensing particles onto a surface of the deposited first material, the first material attaching the sensing particles to the substrate with at least a portion of the sensing particles is exposed to an ambient environment.

11. The method of claim 10, wherein the color changing material that is dispersed into the porous host structure is selected from a group consisting of: bromocresol green, phtalocyanine dye, porphyrin dies, indigo derivatives, azo dyes, anthraquinone dye, triarylmethane dye, transition metal salts that coordinate with gases including palladium chloride, palladium sulfates, ammonium molybdates, and potassium permanganate.

12. The method of claim 10 wherein the porous host structure is an organic polymer.

13. The method of claim 10, wherein the porous host aerogel has a Brunauer Emmett Teller surface areas above 50 $m^2/g$.

14. A method of forming a colorimetric sensor, comprising:
    depositing a first material onto a substrate darker than white substrate;
    providing porous sensing particles by one of one of infusing the aerogel with the sensing species, having the sensing species present in a solvent that is a part of a precursor solution used to form the aerogel, or chemically grafting the sensing species onto aerogel walls during or after forming the aerogel, wherein the sensing particles comprise fluorescence changing sensing species that change their fluorescence in the presence of an analyte dispersed into a porous host structure; and
    embedding the porous sensing particles onto a surface of the deposited first material, the first material attaching the sensing particles to the substrate with that at least a portion of the sensing particles is exposed to an ambient environment.

15. The method of claim 14, wherein the fluorescence changing sensing species change the intensity and the wavelength of the emitted light upon interaction with an analyte.

16. The method of claim 14, wherein the porous host structure is an organic polymer.

* * * * *